United States Patent
Hwang et al.

(10) Patent No.: US 10,329,211 B2
(45) Date of Patent: Jun. 25, 2019

(54) METHOD FOR OLIGOMERIZATION OF ETHYLENE

(71) Applicant: KOREA RESEARCH INSTITUTE OF CHEMICAL TECHNOLOGY, Daejeon (KR)

(72) Inventors: Dong Won Hwang, Daejeon (KR); Ho Jeong Chae, Daejeon (KR); MaEum Lee, Jeollanam-do (KR); Ji Sun Yoon, Gyeonggi-do (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/594,115

(22) Filed: May 12, 2017

(65) Prior Publication Data
US 2017/0327437 A1 Nov. 16, 2017

(30) Foreign Application Priority Data
May 13, 2016 (KR) .................... 10-2016-0059001

(51) Int. Cl.
C07C 2/08 (2006.01)
C07C 2/12 (2006.01)
C07C 2/28 (2006.01)

(52) U.S. Cl.
CPC .................. *C07C 2/12* (2013.01); *C07C 2/28* (2013.01); *C07C 2523/755* (2013.01);
(Continued)

(58) Field of Classification Search
CPC .................................... C07C 2/12; C07C 2/28
(Continued)

(56) References Cited

U.S. PATENT DOCUMENTS 6,444,866 B1  9/2002 Commereuc et al.
9,771,533 B2 * 9/2017 Lilga .................... C10G 29/205
(Continued)

FOREIGN PATENT DOCUMENTS

JP    2010-030902    2/2010
KR    10-2011-0018389    2/2011

OTHER PUBLICATIONS

Hulea, V. et. al. "Ni-exchanged AIMCM-41—An efficient bifunctional catalyst for ethylene oligomerization", Journal of Catalysis, 225 (2004), pp. 213-222. (Year: 2004).*
(Continued)

*Primary Examiner* — Philip Y Louie
*Assistant Examiner* — Aaron W Pierpont
(74) *Attorney, Agent, or Firm* — Norton Rose Fulbright US LLP

(57) ABSTRACT

Methods for the oligomerization of ethylene, and more specifically, methods for the preparation of mainly ethylene oligomers of $C_{10}$ or higher are described. A method can include performing a first oligomerization of an ethylene gas using a Ni-containing mesoporous catalyst, followed by a second oligomerization using an ion exchange resin, etc. to produce ethylene oligomers of $C_{10}$ or higher. The method for the preparation of ethylene oligomers can produce $C_{8-16}$ ethylene oligomers in high yield without inducing deactivation of the catalyst, compared to the conventional technology of ethylene oligomerization by a one-step process.

11 Claims, 10 Drawing Sheets

(52) U.S. Cl.
CPC ...... *C07C 2529/40* (2013.01); *C07C 2529/46* (2013.01); *C07C 2529/70* (2013.01); *C07C 2529/76* (2013.01); *C07C 2531/10* (2013.01)

(58) Field of Classification Search
USPC ........................................ 585/500, 502, 517
See application file for complete search history.

(56) References Cited

U.S. PATENT DOCUMENTS

| | | | | |
|---|---|---|---|---|
| 2005/0258077 | A1* | 11/2005 | Landau | B01J 20/02 208/244 |
| 2008/0027188 | A1* | 1/2008 | Small | B01J 31/143 526/113 |
| 2009/0203947 | A1* | 8/2009 | Schneider | C07C 2/08 585/519 |
| 2011/0124938 | A1* | 5/2011 | Inoue | B01J 23/755 585/533 |
| 2011/0172482 | A1* | 7/2011 | Cabiac | B01J 29/041 585/502 |
| 2011/0288256 | A1* | 11/2011 | Vermeiren | C07C 11/08 526/348.6 |
| 2011/0288352 | A1* | 11/2011 | Peters | C10G 3/42 585/14 |
| 2012/0172645 | A1* | 7/2012 | Sydora | B01J 31/143 585/511 |
| 2014/0179970 | A1* | 6/2014 | Fritz | B01J 31/143 585/513 |
| 2015/0191666 | A1 | 7/2015 | Bradin | |
| 2015/0299069 | A1* | 10/2015 | Azam | C07C 2/36 585/513 |

OTHER PUBLICATIONS

Haynes, W. M. "CRC Handbook of Chemistry and Physics", 95th Edition, Internet Version (2015); pp. 3-298 and 3-386 (Year: 2015).*

Gobara, H. M. "Characterization and catalytic activity of NiO/mesoporous aluminosilicate AlSBA-15 in conversion of some hydrocarbons", Egyptian Journal of Petroleum, 21 (2012), pp. 1-10 (Year: 2012).*

Vasile Hulea et al., "Ni-exchanged AlMCM-41—An efficient bifunctional catalyst for ethylene oligomerization," Journal of Catalysis 225 (2004) 213-222.

* cited by examiner

METHOD FOR OLIGOMERIZATION OF ETHYLENE

CROSS-REFERENCE TO RELATED APPLICATIONS

This application claims the benefit of Korean Patent Application No. 10-2016-0059001, filed May 13, 2016. The contents of the referenced application are incorporated herein by reference.

TECHNICAL FIELD

The present invention relates to a method for the oligomerization of ethylene, and more specifically, to a method for the preparation of mainly ethylene oligomers of $C_{10}$ or higher, which includes obtaining ethylene oligomers of $C_4$ or higher by performing a first oligomerization of an ethylene gas using a Ni-containing mesoporous catalyst, followed by a second oligomerization using an ion exchange resin, etc.

BACKGROUND ART

Recently, there is a growing demand on biojet fuel in an effort to reduce greenhouse gas production. Among various technologies for manufacturing biojet fuel, those which use bioethanol as a raw material have an advantage in that they enable securing a large amount of relatively cheap raw materials.

Jet fuel is required to have a challenging property such as high energy density without being frozen at high altitudes, and in this regard, it is preferred that jet fuel have a distribution of a $C_{4-10}$ composition to secure the above property.

Accordingly, in the technologies for manufacturing jet fuel using bioethanol, the technology of converting the ethylene ($C_2$), which was prepared by ethanol dehydration, into $C_{8-16}$ oligomers is absolutely necessary. The $C_{8-16}$ oligomers prepared as such can be subjected to subsequent hydrogenation and distillation processes, and finally jet-grade fuel can be obtained therefrom.

However, those technologies which convert ethylene into $C_{8-16}$ oligomers by a one-step catalytic reaction have a problem in that they not only have low selectivity to oligomers of $C_{8-16}$ or higher but also oligomers of $C_{10}$ or higher attach to the surface of the catalyst because oligomers of $C_{10}$ or higher are produced at high temperature and thus the catalyst is easily deactivated (Vasile Hulea et al., Journal of Catalysis 225 (2004), 213-222).

Under the circumstances, the present inventors have made efforts to solve the above problems, and as a result, they have discovered that a total of two-step ethylene oligomerization can not only increase the selectivity to oligomers of $C_{10}$ or higher but also prevent the deactivation of the catalyst involved therein, thereby completing the present invention.

SUMMARY OF THE INVENTION

An object of the present invention is to provide a method for efficiently converting ethylene prepared by ethanol dehydration into $C_{8-16}$ oligomers, during the process of manufacturing jet fuel from bioethanol.

To achieve the object, the present invention provides a catalytic process for efficiently preparing $C_{8-16}$ ethylene oligomers from ethylene without the deactivation of the catalyst.

Specifically, a first aspect of the present invention provides a method for the oligomerization of ethylene, in which the method includes:

a first step of oligomerizing $C_2H_4$ comprised in a gaseous stream ethylene at a temperature between 150° C. and 250° C. using a first catalyst to produce a gas containing an ethylene oligomer;

a second step of separating the first mixed gas containing an ethylene oligomer into a second mixed gas containing unconverted $C_2H_4$ and a mixed liquid containing an ethylene oligomer by cooling;

a third step of obtaining a mixed liquid containing a $C_{6-16}$ ethylene oligomer from the mixed liquid containing an ethylene oligomer separated in the second step using a second catalyst; and a fourth step of separating the mixed liquid containing a $C_{6-16}$ ethylene oligomer into a mixed gas containing a $C_6/C_7$ ethylene oligomer and a mixed liquid containing a $C_{8-16}$ ethylene oligomer by distillation at a temperature between 90° C. or higher and below 121° C.

A second aspect of the present invention provides a method for preparing jet fuel, comprising hydrogenating the $C_{8-16}$ ethylene oligomer prepared by the present invention.

The present invention is explained in detail herein below.

The mixed gas containing $C_2H_4$ (ethylene) may be produced by ethanol dehydration of bioethanol.

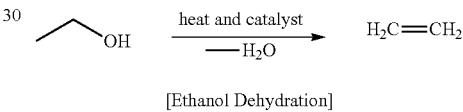

[Ethanol Dehydration]

Alternatively, the mixed gas may be a first mixed gas containing $C_2H_4$ separated from a second step discussed below.

The first step is a step for the oligomerization of ethylene using the first catalyst. The first catalyst may be a mesoporous catalyst containing nickel (Ni). The Ni-containing mesoporous catalyst may be one in which a nickel compound is supported on a mesoporous carrier which contains silica and alumina. The mesoporous carrier is preferably one which contains silica and alumina to the extent that the Si/Al molar ratio is in the range of 0.3 to 50. The mesoporous carrier is preferably an amorphous silica-alumina; a zeolite which is nano-sized or in a nanosponge-type; micro-sized, nano-sized, or polymer-coated and acid-treated SBA-15; MCM-41, etc., but is not limited thereto.

Although the Ni content of the Ni-containing mesoporous catalyst may be determined based on the amount of aluminum contained in the porous carrier, the Ni content is preferably in the range of 0.5 wt % to 3 wt % based on the weight of the porous carrier. When the Ni content is less than 0.5 wt %, the conversion into ethylene oligomers may be low, whereas when the Ni content exceeds 3 wt %, the selectivity of oligomers of $C_6$ or higher may be low.

Preferably, the Ni/Al molar ratio in the catalyst may be in the range of 0.1 to 0.5. When the Ni/Al molar ratio is less than 0.1, the conversion into ethylene oligomers may be low, whereas when the Ni/Al molar ratio exceeds 0.5, the selectivity to oligomers of $C_6$ or higher may be low.

The first step is preferably performed at a temperature of 150° C. to 250° C. When the temperature is lower than 150° C., the conversion into ethylene oligomers may be low, whereas when the temperature is higher than 250° C., the selectivity on ethylene oligomers of $C_6$ or higher may be low due to ethylene cracking.

The first step is preferably performed at a pressure of 0.1 MPa to 3 MPa. When the pressure is lower than 0.1 MPa, the conversion into ethylene oligomers may be low, whereas when the pressure is higher than 3 MPa, the catalyst may be rapidly deactivated due to excess formation of ethylene oligomers with a high boiling point.

The first mixed gas containing ethylene oligomers obtained in the first step may include unconverted $C_2H_4$ (ethylene) and ethylene oligomers of $C_4$ or higher.

The first step may preferably include a step of preparing a mixed gas containing ethylene oligomers of $C_4$ or higher by performing oligomerization at about 150° C. after injecting an ethylene gas into a fixed-bed catalytic reactor filled with a Ni-containing mesoporous catalyst.

The second step may be a step for separating the second mixed gas containing the unconverted $C_2H_4$ from the first mixed gas by cooling the first mixed gas containing ethylene oligomers obtained from the first step.

The cooling temperature of the second step may be adjusted according to the boiling point of the ethylene oligomers to be separated.

Preferably, the second step may include a step of separating a mixed liquid containing ethylene oligomers of $C_4$ or higher from the second mixed gas containing unconverted $C_2H_4$, by cooling the first mixed gas containing ethylene oligomers to the boiling point (−6.47° C.) of $C_4$ ethylene oligomers, i.e., 1-butene, or lower. The second mixed gas may include a $C_4$ ethylene oligomer gas according to the difference in temperature during the cooling process.

The third step is a reaction step for the dimerization of the ethylene oligomers separated from the second step, and the second catalyst is used in this step. It is preferred that an ion exchange resin-type Brønsted solid acid catalyst such as Amberlyst-35 or a Lewis solid acid catalyst, in which aluminum is substituted in the mesoporous material such as H-beta zeolite, SBA-15, and MCM-41, be used as the second catalyst, but the second catalyst is not limited thereto.

The third step may be a step for obtaining a mixed liquid containing $C_{6-16}$, as a result of the dimerization of the ethylene oligomers separated from the second step. For this purpose, the third step is preferably performed at a temperature of 50° C. to 150° C. When the temperature is lower than 50° C., an ethylene oligomer liquid of lower than $C_6$ may form, whereas when the temperature is higher than 150° C., the ethylene oligomers of $C_6$ or higher may be gasified, and is thus not preferred.

The third step is preferably performed at a pressure of 0.1 MPa to 5 MPa. When the pressure is lower than 0.1 MPa, the selectivity to the oligomers of $C_{10}$ or higher may be low, whereas when the pressure is higher than 5 MPa, the catalyst may be rapidly deactivated due to excess formation of ethylene oligomers with a high boiling point.

The fourth step may be a step for separating ethylene oligomers of lower than $C_8$ from the mixed liquid containing $C_{6-16}$ ethylene oligomers obtained from the third step.

In an exemplary embodiment, the fourth step may be a step for separating ethylene oligomers of $C_8$ or higher by distillation of the mixed liquid containing $C_{6-16}$ ethylene oligomers obtained from the third step at a temperature (94° C. or higher) enabling vaporization of $C_6$ ethylene oligomers.

Preferably, the fourth step may be performed at a temperature ranging from 90° C. or higher to lower than 121° C. and at an atmospheric pressure.

In the present invention, the first catalyst for ethylene oligomerization and the second catalyst for ethylene oligomerization are characterized in that they are recycled without being deactivated. This is because the ethylene oligomerization method of the present invention not only has high selectivity to the oligomers of $C_{10}$ or higher but also prevents the attachment of the oligomers of $C_{10}$ or higher to the surface of the catalyst due to the production of oligomers of $C_{10}$ or higher at low temperatures.

In another exemplary embodiment of the present invention, the mixed gas containing $C_6/C_7$ ethylene oligomers separated from the fourth step may be concentrated to a temperature of 63° C. or below, preferably to 50° C. or below, at which the liquefaction of $C_6$ ethylene oligomers can occur, and converted into a liquid, and supplied to the second step to be used for the production of a mixed liquid containing ethylene oligomers.

Advantageous Effects of the Invention

The method for the preparation of ethylene oligomers according to the present invention can produce $C_{8-16}$ ethylene oligomers in high yield without inducing deactivation of the catalyst, compared to the conventional technology of ethylene oligomerization by a one-step process.

Additionally, according to the present invention, an unconverted ethylene-containing mixed gas and low-grade ethylene oligomers can be separated and recycled during the reaction process thereby improving the process efficiency and reducing the process cost.

DETAILED DESCRIPTION OF THE INVENTION

Hereinafter, the present invention will be described in more detail with reference to the following Examples. However, these Examples are for illustrative purposes only and the invention is not intended to be limited by these Examples.

Figure 1:
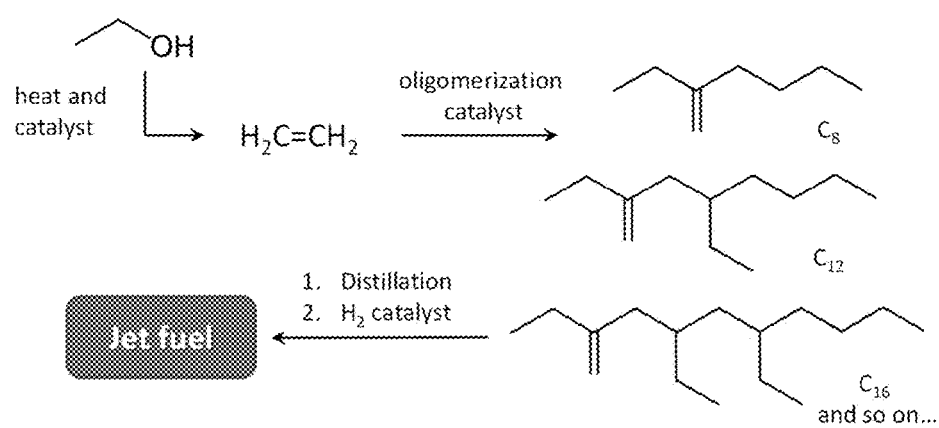
FIG. 1 shows a reaction mechanism and a reaction flow with respect to the preparation of jet fuel from ethanol.
Figure 2:
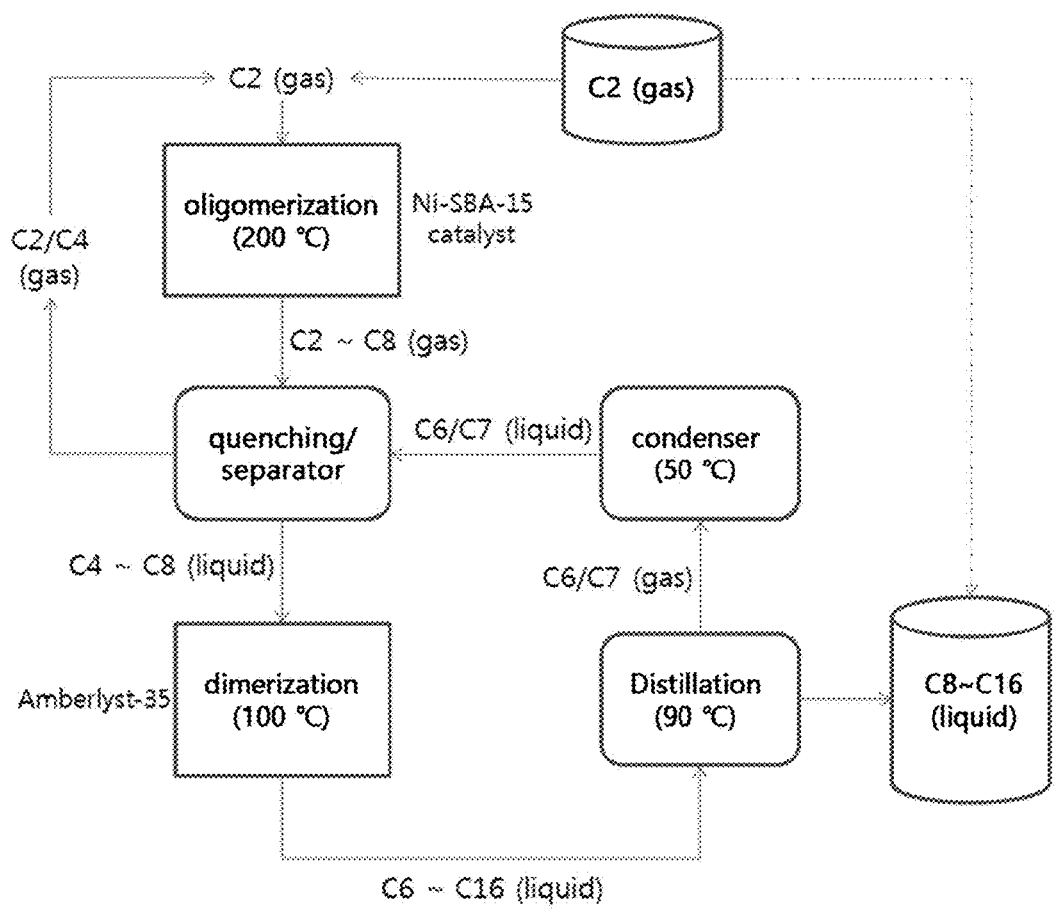
FIG. 2 shows a flowchart illustrating the method of ethylene oligomerization according to an exemplary embodiment of the present invention.
Figure 3:
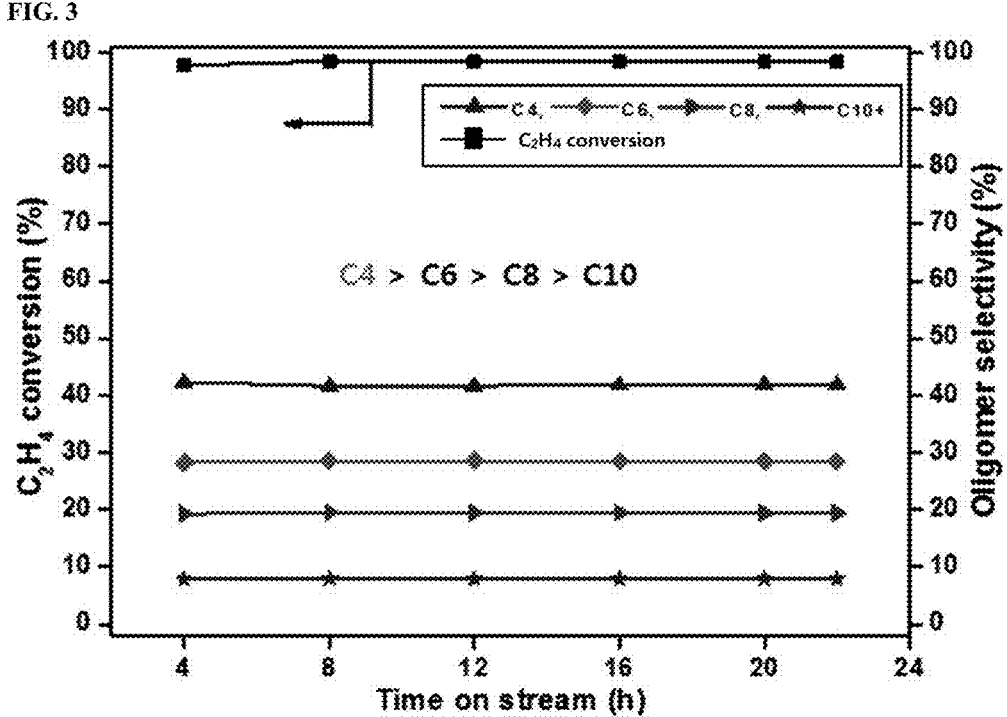
FIG. 3 shows a graph illustrating the ethylene conversion according to time and the change in oligomer selectivity in the first step of Example 1.

<Example 1> Ethylene Oligomerization Using Ni-SBA-15 Catalyst and Amberlyst-35 Catalyst A fixed-bed reactor was filled with Ni-SBA-15 (Si/Al molar ratio=5, 1 g) and pretreated in an atmospheric pressure at 550° C. while flowing a nitrogen gas thereto at 60 mL/min for 8 hours. Then, the reactor was maintained at a temperature of 200° C. and at a pressure of 10 bar. Subsequently, the reaction was performed while flowing ethylene thereto at 8 mL/min (the first step). During the reaction for 200 hours in the above conditions, the catalytic activity was continuously maintained at a high level of 98% or above without a change in ethylene conversion. As shown in FIG. 3, it was confirmed that the product distribution was in the order of $C_4 > C_6 > C_8 > C_{10}$, and the yield of the oligomers of $C_{10}$ or higher was lower than 10%.

The gas product obtained in the first step was cooled to 5° C. to separate the liquid product therefrom.

Figure 4:
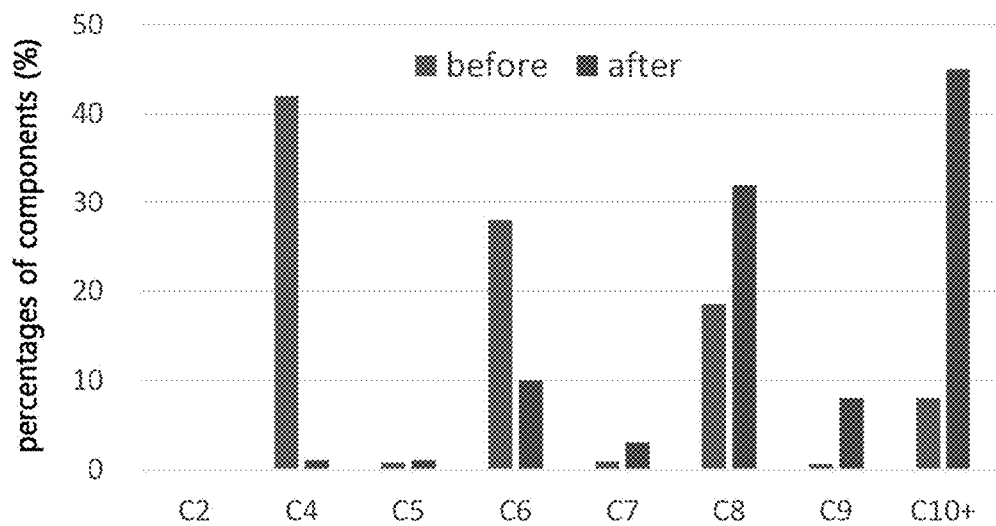
FIG. 4 shows a graph illustrating the results of product analysis after the reaction for 24 hours in the second step of Example 1.

The liquid product obtained from the first step in an amount of 10 g was mixed with 0.5 g of the Amberlyst-35 ion exchange resin, and the reactor was maintained at a temperature of 100° C. and at a pressure of 30 bar. As shown in FIG. 4, as a result of the product analysis of the 24 hour-reaction, the percentage of $C_4$ components was significantly decreased while the percentages of $C_8$ and $C_{10}$ components were significantly increased instead. In particular, the percentage of the components of $C_{10}$ or higher was increased from 8% before the reaction to 45% after the reaction.

The resulting product was distilled at 90° C. at atmospheric pressure to obtain a gas product and a liquid product.

<Example 2> Ethylene Oligomerization Using Ni-SBA-15 Catalyst and H-Beta Zeolite Catalyst Ethylene oligomerization was performed in the same manner as in Example 1, except that the liquid product obtained in the first step was mixed with H-beta zeolite (0.5 g) instead of Amberlyst-35 ion exchange resin and then the reactor was maintained at a temperature of 200° C. and at a pressure of 30 bar.

Figure 5:
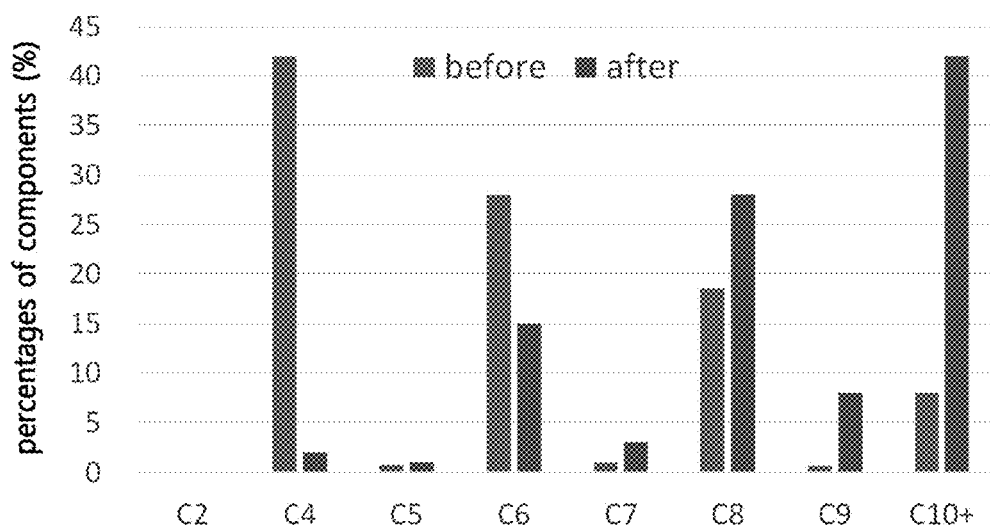
FIG. 5 shows a graph illustrating the results of product analysis after the reaction for 24 hours in the second step of Example 2.

As shown in FIG. 5, as a result of the product analysis of the 24 hour-reaction, the percentage of $C_4$ components was significantly decreased while the percentages of $C_8$ and $C_{10}$ components were significantly increased instead. In particular, the percentage of the components of $C_{10}$ or higher was increased from 8% before the reaction to 42% after the reaction for 24 hours.

Figure 6:
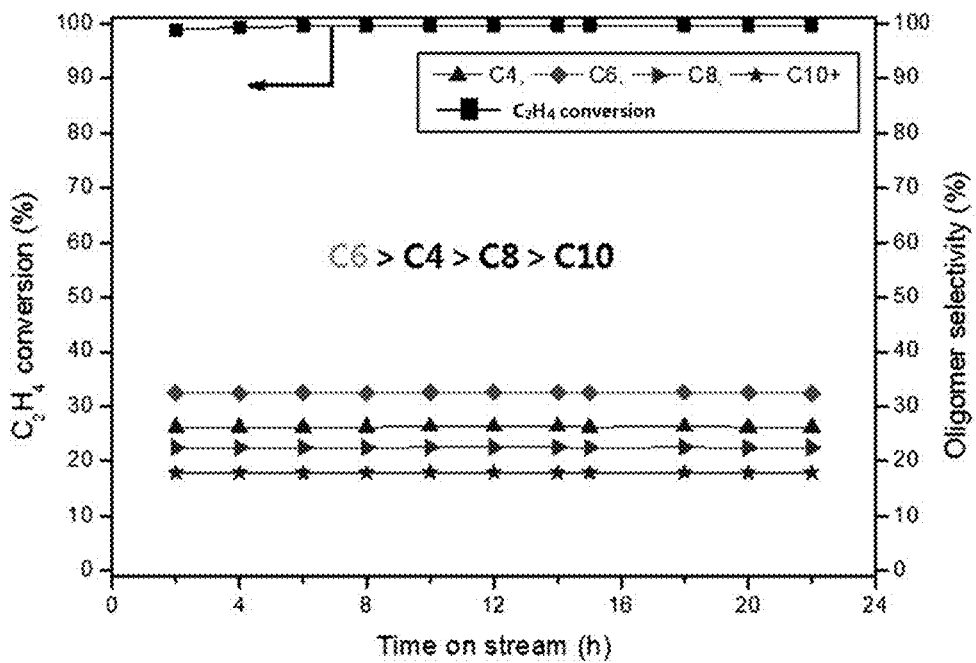
FIG. 6 shows a graph illustrating the ethylene conversion according to time and the change in oligomer selectivity in the first step of Example 3.

<Example 3> Ethylene Oligomerization Using Ni/SIRAL 30 Catalyst and Amberlyst-35 Catalyst After filling a fixed-bed reactor with Ni/SIRAL 30 (Si/Al molar ratio=0.3, 1 g), a reaction was performed in the same manner as in Example 1 while flowing ethylene thereto at 5 mL/min, and thereby the liquid product of the first step was obtained. In the above conditions, ethylene conversion was maintained at a high level of 98% or higher. As shown in FIG. 6, it was confirmed that the product distribution was in the order of $C_6 > C_4 > C_8 > C_{10}$, and the yield of the oligomers of $C_{10}$ or higher was about 18%.

The gas product obtained in the first step was cooled to 5° C. to separate the liquid product therefrom.

Figure 7:
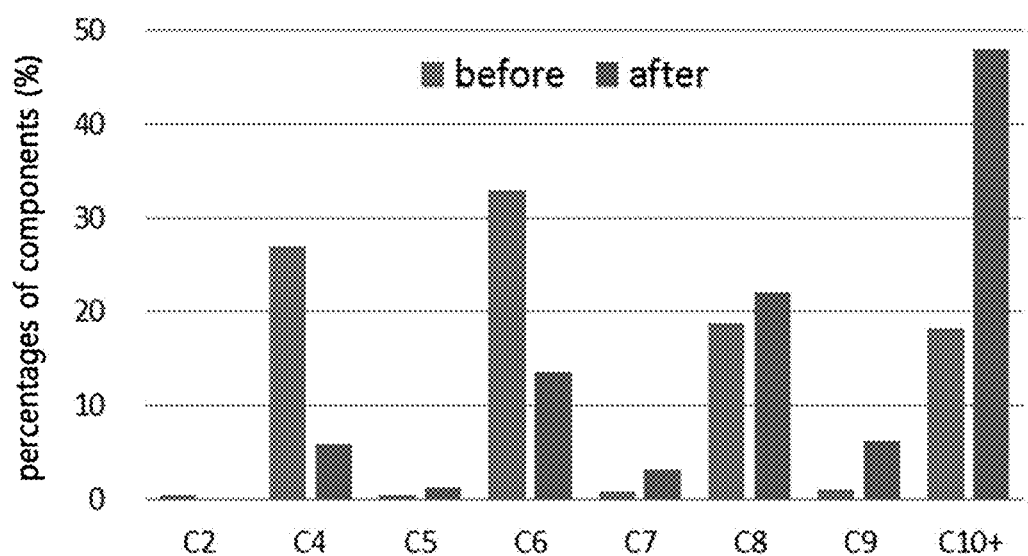
FIG. 7 shows a graph illustrating the results of product analysis after the reaction for 24 hours in the second step of Example 3.

The liquid product obtained from the first step in an amount of 10 g was mixed with 0.5 g of the Amberlyst-35 ion exchange resin, and a reaction was performed in the same manner as in Example 1. As shown in FIG. 7, as a result of the product analysis of the 24 hour-reaction, the percentage of $C_4$ components was significantly decreased while the percentages of $C_8$ and $C_{10}$ components were significantly increased instead. In particular, the percentage of components of $C_{10}$ or higher was significantly increased to about 48%.

The resulting product was distilled at 90° C. at atmospheric pressure to obtain a gas product and a liquid product.

<Example 4> Ethylene Oligomerization Using Ni/Zeolite Catalyst

Figure 8:
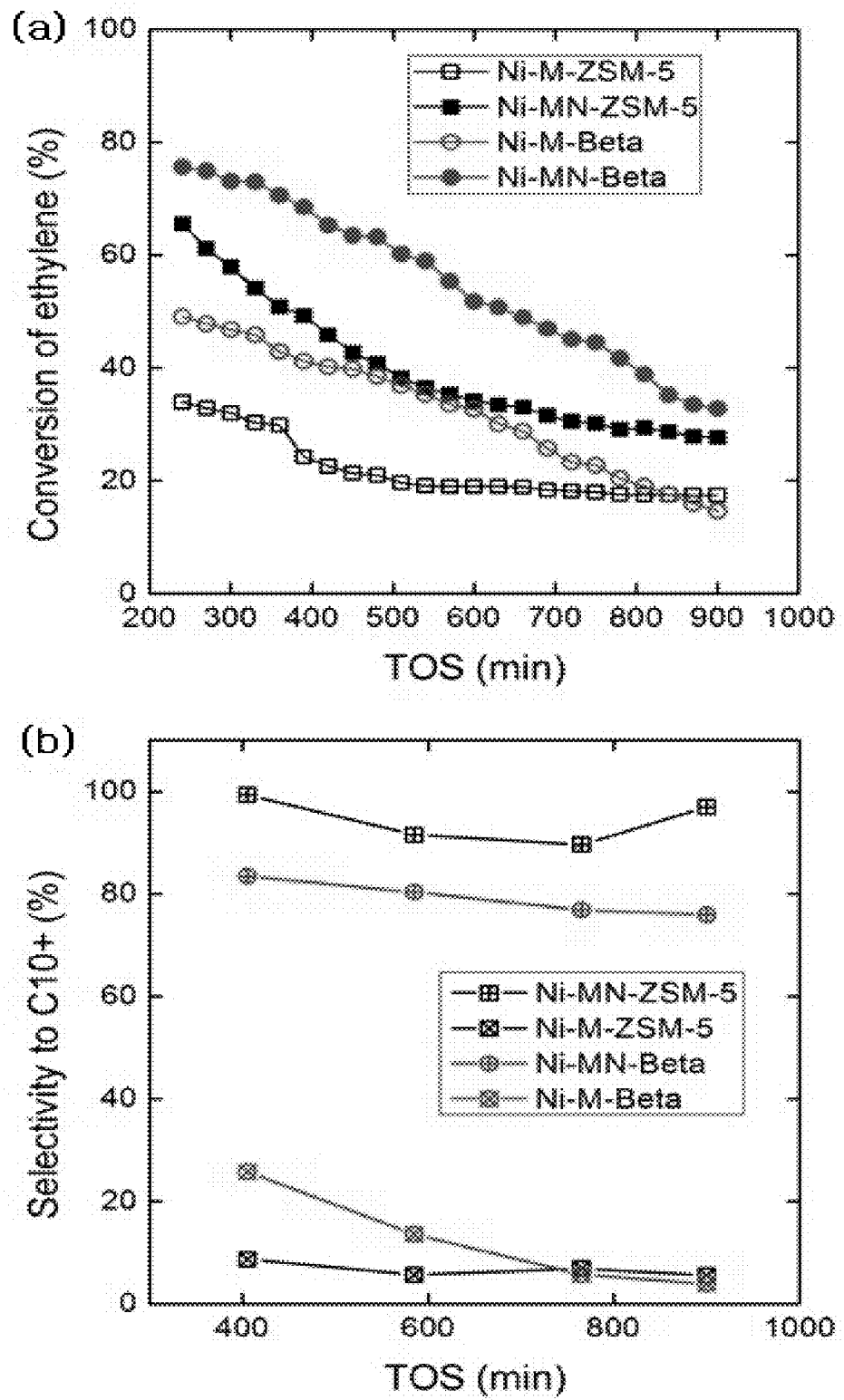
FIG. 8 shows graphs illustrating the ethylene conversion according to time and the change in selectivity to oligomers of $C_{10}$ or higher in the liquid-phase product of Example 4.

A fixed-bed reactor was filled with Ni-ZSM-5 and Ni-beta zeolites (Si/Al molar ratio=50, 0.2 g each) and pretreated in an atmospheric pressure at 550° C. while flowing a helium gas thereto at 20 mL/min for 8 hours. In particular, with respect to the zeolite catalysts used herein (ZSM-5 and beta zeolite), nickel was supported in an amount of about 1 wt % to a micro-sized (M-)-type zeolite and a nanosponge-type zeolite having mesoporous pores (MN-). Then, the reactor was cooled to 200° C. and the pressure of the entire reactor was adjusted to 35 bar using a back pressure regulator while flowing a helium gas thereto at 200 mL/min. Subsequently, a reaction was performed for about 900 minutes by injecting an argon gas, an inert gas, to the reactor at 10 mL/min while simultaneously flowing ethylene thereto at 6.6 mL/min (the first step). For the separation of the liquid product released after the reaction, a cooler (5° C.) was provided under the reactor. The liquid-phase and gas-phase products among the reaction products were collected at 3 hour intervals, subjected to gas chromatography mass analyzer for the analysis of each component, and ethylene conversion and selectivity on the oligomers of $C_{10}$ or higher in the liquid-phase product were drawn and the results are shown in FIG. 8. As devices for the analysis, YL Instrument 6500 GC System equipped with a DHA capillary column (100 m, 0.25 mm, 0.5 μm) was used as the gas chromatography column.

As shown in FIG. 8, the catalyst provided as nano-sized particles having a nanosponge structure among the ZSM-5 zeolite containing about 1 wt % of nickel, exhibited excellent ethylene conversion and selectivity on oligomers of $C_{10}$ or higher, whereas the catalyst provided as micro-sized particles exhibited slight ethylene conversion, although significantly lower than that of the catalyst provided as nano-sized particles, and the selectivity on the oligomers of $C_{10}$ or higher was shown to be low to be less than 10%. These results suggest that the catalyst provided as micro-sized particles can induce the oligomerization reaction of ethylene but it only enables the production of about $C_{4-6}$ hydrocarbons and has a difficulty in producing high-value added hydrocarbons of $C_{10}$ or higher.

<Example 5> 1-Hexene Oligomerization Using Zeolite Catalyst

As a method for compensating the drawbacks of the one-step ethylene oligomerization in Example 4, a two-step oligomerization was performed. In this regard, 1-hexene was assigned as a model compound, and the two-step oligomerization was performed. For the zeolite catalyst, ZSM-5 and beta-zeolite having a Si/Al molar ratio of 50 were used, and solid acid catalysts in a micro-sized-type zeolite (M-), a nano-sized-type zeolite (N-) and a nanosponge-type zeolite having mesoporous pores (MN-) were used.

Figure 9:
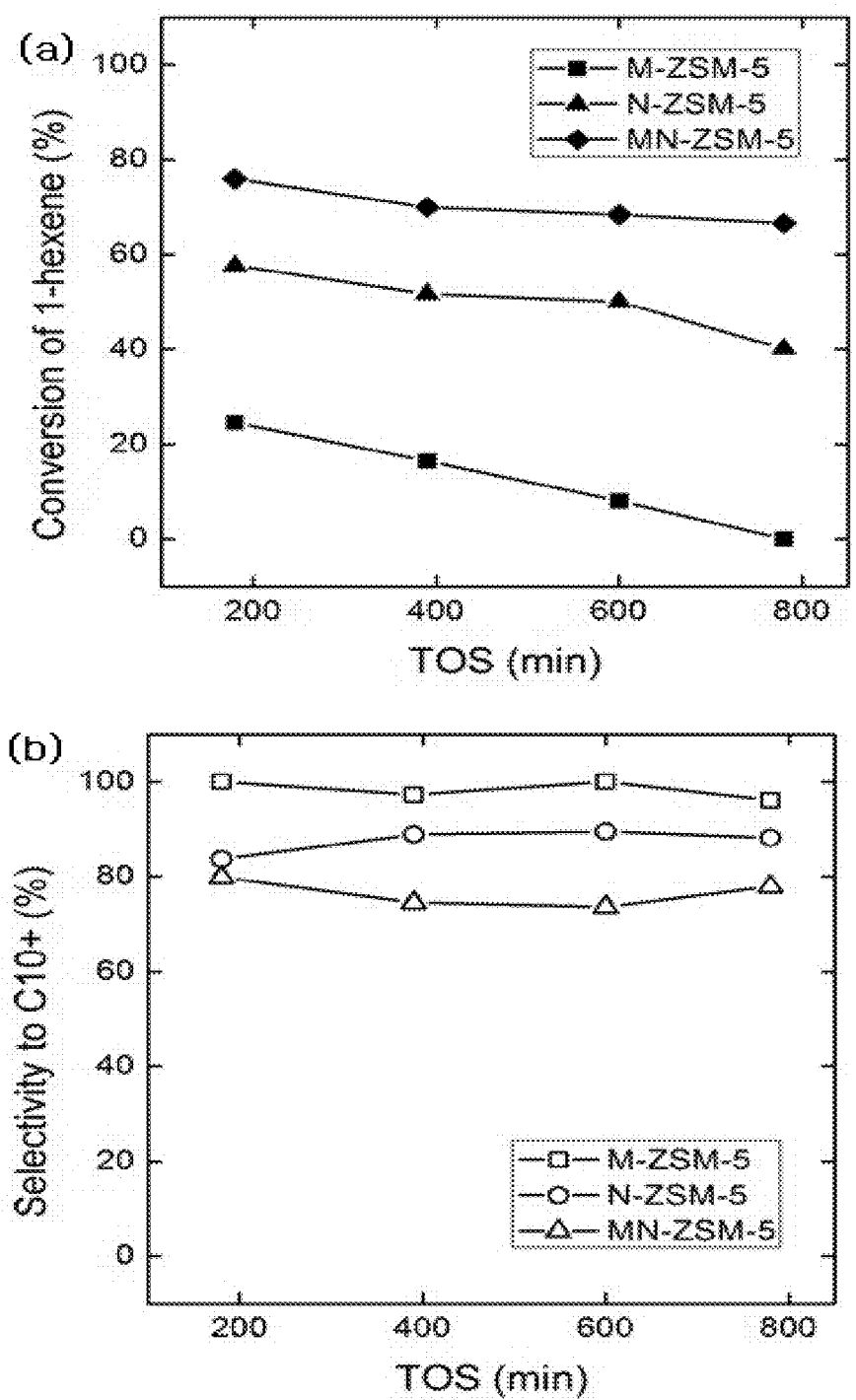
FIGS. 9 and 10 show graphs illustrating the 1-hexene conversion according to time and the change in selectivity to oligomers of $C_{10}$ or higher in the liquid-phase product of Example 5, respectively.
Figure 10:
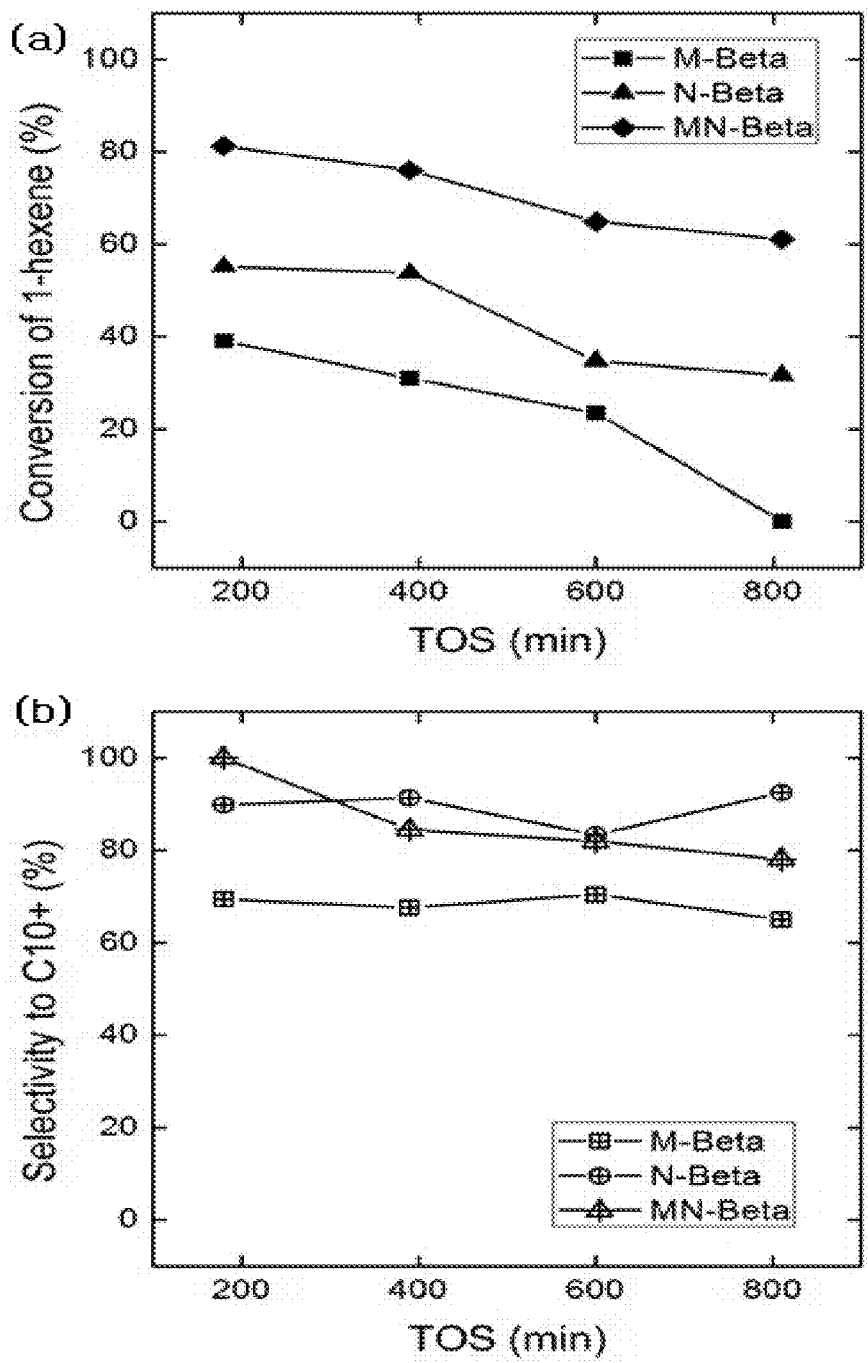

A fixed-bed reactor was filled with a zeolite catalyst (0.5 g), pretreated in the same manner as in Example 4, and the temperature and pressure of the reactor were adjusted. Then, the reaction was started while flowing a mixed solution of 1-hexene (95 wt %) and n-heptane (5 wt %) at a rate of 0.025 mL/min, in a weight/hour space velocity (WHSV) of 2 h$^{-1}$, using an HPLC pump, and the reaction was continued for about 780 minutes. For the separation of the liquid product released after the reaction, a cooler (5° C.) was provided under the reactor. The liquid-phase product among the reaction products was collected at 3 hour intervals, analyzed in the same manner as in Example 4 using the same gas chromatography mass analyzer and column, and the results are shown in FIGS. 9 and 10.

The values of peak areas were drawn from the gas chromatogram obtained therefrom and were compared with the existing values obtained by quantification of the expected products. The values of the peak areas after the reaction were calculated by comparing with the existing values of the peak areas of the expected products based on the value of the n-heptane, which was not involved in the reaction, and thereby the conversion was measured and the selectivity on oligomers of $C_{10}$ or higher was drawn based on the result. As shown in FIGS. 9 and 10, the micro-sized particles of ZSM-5 and beta-zeolites not only exhibited significantly low conversion of 1-hexene and selectivity on oligomers of $C_{10}$ or higher compared to the nano-sized particles but also showed a further decrease in the conversion of 1-hexene and selectivity on oligomers of $C_{10}$ or higher along with the increase of the reaction time and exhibited absolutely no activity at all after the lapse of 800 minutes of the reaction time. Meanwhile, in the case of the nano-sized particles, they showed significantly higher conversion of 1-hexene and selectivity on oligomers of $C_{10}$ or higher compared to the micro-sized particles, and in particular, the particles having a nanosponge structure were shown to have even higher conversion of 1-hexene and selectivity on oligomers of $C_{10}$ or higher. The result indicates that even a size reduction of the particle to a nano level can significantly improve the catalytic activity of olefin, e.g., 1-hexene, with regard to the oligomerization and selectivity on oligomers of $C_{10}$ or higher, and furthermore, in a case when a sponge type microstructure is added thereto, a more significant effect can be provided.

<Example 6> 1-Hexene Oligomerization Using SBA-15 Catalyst

As a method for compensating the drawbacks of the one-step ethylene oligomerization, a two-step oligomerization was performed by assigning 1-hexene as a model compound in the same manner as in Example 5. As the SBA-15 catalyst, micro-sized and nano-sized (H-SBA-15, 400 nm) ones were used. For the purpose of lowering the process temperature, polymer coated and acid treated SBA-15 (H-PS/SBA-15), which was prepared by coating SBA-15 with a H-PS (polystyrene) followed by addition of acid, was used.

Figure 11:
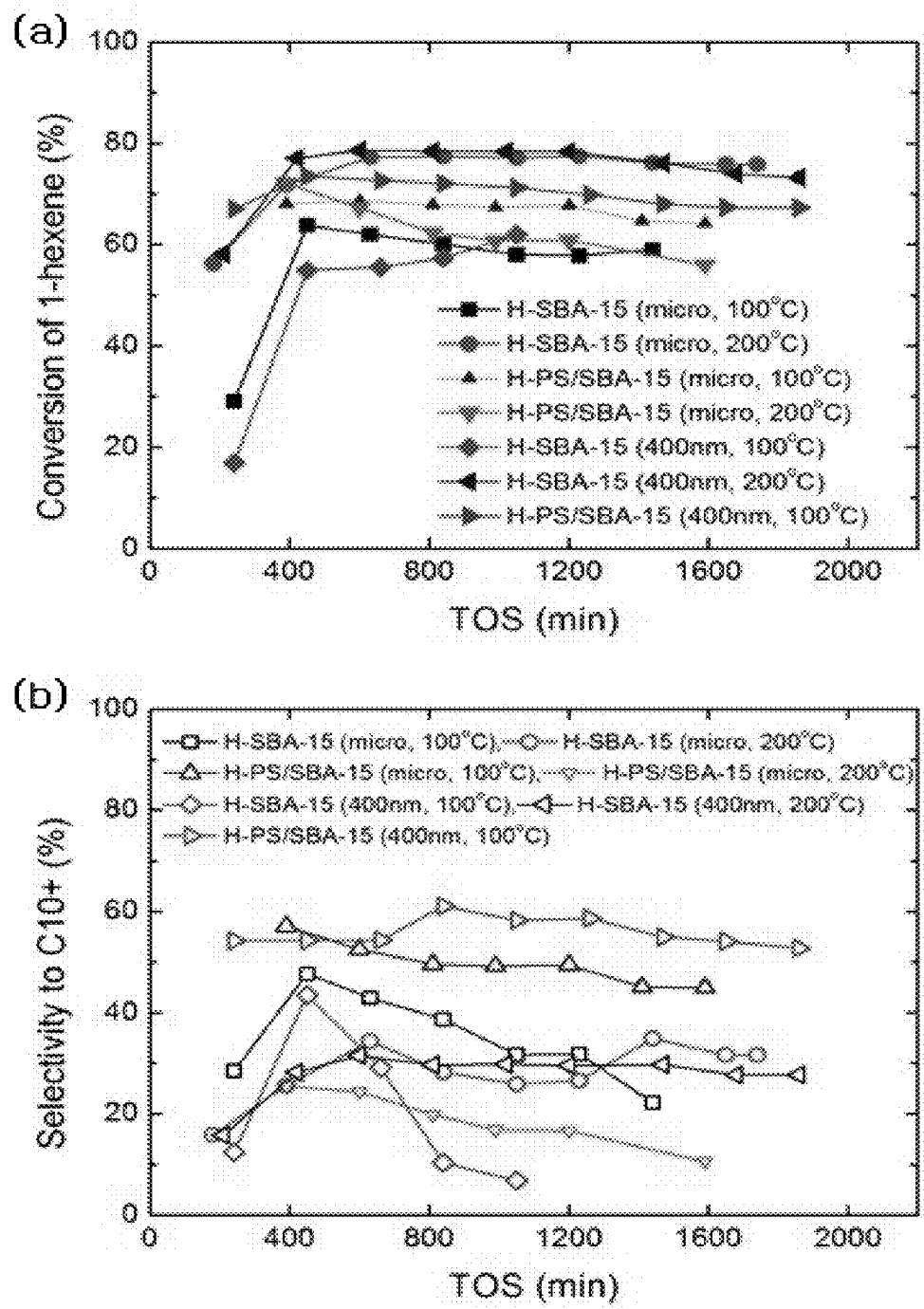
FIG. 11 shows graphs illustrating the 1-hexene conversion according to time and the change in selectivity to oligomers of $C_{10}$ or higher in the liquid-phase product of Example 6.

In the case of the H-SBA-15 catalyst, the catalyst (2 g) was filled into the fixed-bed reactor and then pretreated in the same manner as in Example 4, and the temperature and pressure of the reactor were adjusted. In the case of the H-PS/SBA-15 catalyst, the same amount of the catalyst (2 g) was filled into the fixed-bed reactor and then the reactor was heated at a rate of 5° C./min to 100° C. while flowing a helium gas at a rate of 50 mL/min thereto. After maintaining the reactor at 100° C. for 3 hours, the temperature was adjusted according to the reaction conditions. Then, the reaction was started while flowing a mixed solution of 1-hexene (95 wt %) and n-heptane (5 wt %) at a rate of 0.1 mL/min, in a weight/hour space velocity (WHSV) of 2 h$^{-1}$, using an HPLC pump, and the reaction was continued for about 190 minutes. For the separation of the liquid product released after the reaction, a cooler (5° C.) was provided under the reactor. The product in liquid-phase among the reaction products was collected at 3 hour intervals, analyzed in the same manner as in Examples 4 and 5 using the same gas chromatography mass analyzer and column and calculated, and the results are shown in FIG. 11.

A 1-hexene oligomerization reaction was performed using a series of catalysts, which were prepared by coating micro-sized SBA-15 and SBA-15 of a size of 400 nm with polystyrene and activated by acid treatment, and a catalyst, which was prepared by acid treatment of SBA-15 itself which was not coated with a polymer. The conversion according to reaction time was calculated and the results are shown in FIG. 11. The reaction was performed not only at 100° C. but also at 200° C. by elevating the temperature, and the conversion and selectivity on the oligomers of $C_{10}$ or higher were measured. As a result, it was confirmed that the 1-hexene oligomerization performed using SBA-15, the catalysts (micro-sized and a size of 400 nm) treated with an acid without polymer coating not only exhibited a significantly lower conversion at 100° C. compared to when the reaction was performed at 200° C., but also exhibited a decrease in conversion along with time. In contrast, when the reaction was performed using the SBA-15 catalyst, which was prepared according to the present invention by polystyrene coating followed by acid treatment, it was confirmed that the reaction performed even at 100° C. was shown to achieve conversion at a level similar to that performed at 200° C. This indicates that the use of the catalyst according to the present invention can exhibit the desired conversion of 1-hexene oligomerization without excessively increasing the temperature and thus confirms that the catalyst is an efficient catalyst from the energy aspect.

<Comparative Example 1> Low-Temperature High-Pressure Ethylene Oligomerization Using the Catalyst Ni-SBA-15 Alone A fixed-bed reactor was filled with Ni-SBA-15 (Si/Al molar ratio=5) 1 g and pretreated at atmospheric pressure at a temperature of 550° C. while flowing nitrogen gas thereto at 60 mL/min for 8 hours. Then, the temperature of the reactor was maintained at 120° C. and the pressure of the reactor was maintained at 35 bar. Subsequently, the reaction was proceeded while flowing ethylene at a rate of 5 mL/min thereto.

When the ethylene oligomerization is performed in a high-pressure condition of 35 bar as in this experiment, the selectivity to oligomers of $C_{10}$ or higher may increase.

However, in the above conditions, desorption of the oligomers of $C_{10}$ or higher on the surface of the catalyst may not readily occur and thus the catalyst may be inactivated.

Figure 12:
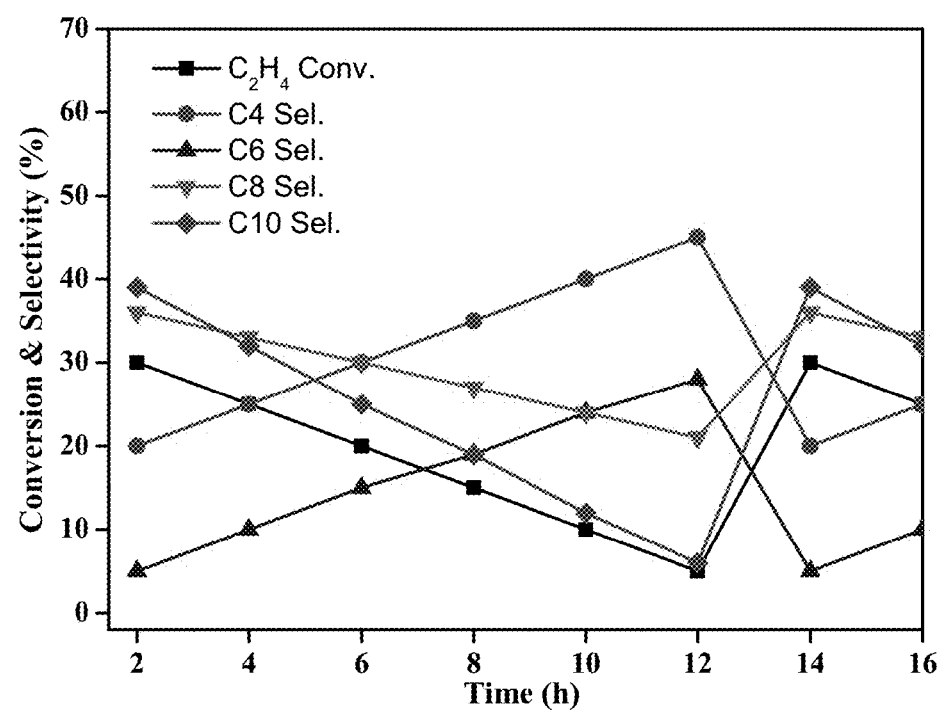
FIG. 12 shows a graph illustrating the ethylene conversion according to time and the change in oligomer selectivity of Comparative Example 1.

As shown in FIG. 12, as a result of the reaction in the above condition, ethylene conversion was decreased from 30% at the initial stage with the increase of reaction time and further decreased to 5%, after 12 hours of the reaction.

Additionally, the $C_{10}$ concentration was as high as 40% at the initial stage of the reaction but decreased to a level of 10% in 12 hours thereafter by the inactivation of the catalyst.

Accordingly, when the reaction is performed in a low-temperature high-pressure condition as in this experiment using the Ni-SBA-15 catalyst alone, ethylene conversion becomes low and the inactivation of the catalyst can rapidly occur and thus it is not possible to obtain the product with high $C_{10}$ concentration on a stable basis.

From the results of the above experiments, it was confirmed that when the conversion of ethylene into oligomers is performed by a two-step process, it can produce $C_{8-16}$ ethylene oligomers in high yield without inducing the inactivation of the catalyst.

The invention claimed is:

1. A method for oligomerization of ethylene, comprising:
    a first step of oligomerizing ethylene in a gas containing ethylene at a temperature between 150° C. and 250° C. and a pressure between 0.1 MPa and 3 MPa in the presence of a first catalyst to produce a gas containing an ethylene oligomer, wherein the first catalyst is a Ni-containing mesoporous catalyst comprising a mesoporous carrier containing silica and alumina in a Si/Al molar ratio between 0.3 and 50;
    a second step of separating the gas containing the ethylene oligomer into a gas containing unconverted ethylene and a liquid containing an ethylene oligomer of $C_4$ or higher by cooling the gas containing the ethylene oligomer;
    a third step of oligomerizing the ethylene oligomer of $C_4$ or higher in the liquid containing the ethylene oligomer of $C_4$ or higher at a temperature of 50° C. to 140° C. in the presence of a second catalyst to produce a liquid containing a $C_{6-16}$ ethylene oligomer, wherein the liquid containing the $C_{6-16}$ ethylene oligomer contains at least one ethylene oligomer of lower than $C_8$ and at least one $C_{8-16}$ ethylene oligomer, wherein the second catalyst is an Amberlyst-35 ion exchange resin catalyst or a Lewis solid acid catalyst; and
    a fourth step of separating the liquid containing the $C_{6-16}$ ethylene oligomer into a gas containing the at least one ethylene oligomer of lower than $C_8$ and a liquid containing at least one $C_{8-16}$ ethylene oligomer by distillation at a temperature between 90° C. and below 121° C.

2. The method of claim 1, wherein the gas containing ethylene in the first step is produced by dehydration of bioethanol.

3. The method of claim 1, wherein the gas containing ethylene in the first step comprises the gas containing unconverted ethylene separated from the second step.

4. The method of claim 1, wherein the mesoporous carrier is amorphous silica-alumina, a nano-sized zeolite, a nano-sponge zeolite, micro-sized SBA-15, nano-sized SBA-15, polymer-coated and acid-treated SBA-15, or MCM-41.

5. The method of claim 1, wherein the nickel content of the Ni-containing mesoporous catalyst is between 0.5 wt % and 3 wt % based on the weight of the mesoporous carrier.

6. The method of claim 1, wherein the Ni/Al molar ratio in the Ni-containing mesoporous catalyst is in the range of 0.1 to 0.5.

7. The method of claim 1, wherein the second step comprises a step of separating the gas containing the ethylene oligomer into the liquid containing the ethylene oligomer of $C_4$ or higher and the gas containing unconverted ethylene by cooling to room temperature or below.

8. The method of claim 1, wherein the third step is performed at a pressure between 0.1 MPa and 5 MPa.

9. The method of claim 1, wherein the fourth step is performed at atmospheric pressure.

10. The method of claim 1, wherein the gas containing the at least one ethylene oligomer of lower than $C_8$ is condensed to a liquid containing the at least one ethylene oligomer of lower than $C_8$ at a temperature of at most 50° C., and wherein the liquid containing the at least one oligomer of lower than $C_8$ is recycled to the second step.

11. The method of claim 1, further comprising hydrogenating the at least one $C_{8-16}$ ethylene oligomer to produce a jet fuel.

* * * * *